US008744783B2

(12) United States Patent
Templeman

(10) Patent No.: US 8,744,783 B2
(45) Date of Patent: Jun. 3, 2014

(54) SYSTEM AND METHOD FOR MEASURING POWER GENERATED DURING LEGGED LOCOMOTION

(75) Inventor: Robert E. Templeman, Bloomington, IN (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 347 days.

(21) Appl. No.: 12/548,996

(22) Filed: Aug. 27, 2009

(65) Prior Publication Data

US 2011/0054809 A1    Mar. 3, 2011

(51) Int. Cl.
| G01L 1/00 | (2006.01) |
| G01L 3/00 | (2006.01) |
| G01L 5/00 | (2006.01) |
| G01R 21/00 | (2006.01) |
| G01R 21/06 | (2006.01) |
| G01P 15/00 | (2006.01) |
| H03F 1/26 | (2006.01) |
| H04B 15/00 | (2006.01) |

(52) U.S. Cl.
USPC ............. 702/44; 702/41; 702/60; 702/141; 702/189

(58) Field of Classification Search
USPC ................ 702/44, 41, 60, 141, 189
See application file for complete search history.

(56) References Cited

U.S. PATENT DOCUMENTS

| 4,703,217 A | 10/1987 | Ratzlaff et al. |
| 4,814,661 A * | 3/1989 | Ratzlaff et al. ............... 310/328 |
| 5,372,365 A | 12/1994 | McTeigue et al. |
| 5,373,651 A | 12/1994 | Wood |
| 5,471,405 A | 11/1995 | Marsh |
| 5,524,637 A | 6/1996 | Erickson |
| 5,619,186 A * | 4/1997 | Schmidt et al. ............ 340/573.1 |
| 5,678,448 A * | 10/1997 | Fullen et al. .................... 73/172 |
| 5,720,200 A | 2/1998 | Anderson et al. |
| 5,925,001 A | 7/1999 | Hoyt et al. |
| 5,955,667 A * | 9/1999 | Fyfe ................................ 73/490 |
| 6,122,846 A | 9/2000 | Gray et al. |
| 6,301,964 B1 | 10/2001 | Fyfe et al. |
| 6,356,856 B1 | 3/2002 | Damen et al. |
| 6,360,597 B1 | 3/2002 | Hubbard, Jr. |
| 6,493,652 B1 | 12/2002 | Ohlenbusch et al. |
| 6,498,994 B2 | 12/2002 | Vock et al. |
| 6,513,381 B2 | 2/2003 | Fyfe et al. |
| 7,171,331 B2 | 1/2007 | Vock et al. |
| 7,225,565 B2 | 6/2007 | DiBenedetto et al. |

(Continued)

OTHER PUBLICATIONS

Morris, S. J., Paradiso, J.A., "A Compact Wearable Sensor Package for Clinical Gait Monitoring", Offspring, vol. 1, No. 1, pp. 7-15, Jan. 31, 2003.

(Continued)

*Primary Examiner* — John Breene
*Assistant Examiner* — Manuel Rivera Vargas
(74) *Attorney, Agent, or Firm* — Christopher A. Monsey

(57) ABSTRACT

A system and method is provided for calculating power generated by a body during legged locomotion. The system includes at least one accelerometer to measure acceleration of the body during legged locomotion, at least one force sensor to measure a plurality of propulsive force impulses created by the body during legged locomotion, and a processor configured to calculate the power generated by the body during legged locomotion using output signals from both the at least one accelerometer and the at least one force sensor.

43 Claims, 10 Drawing Sheets

(56) References Cited

U.S. PATENT DOCUMENTS

| | | |
|---|---|---|
| 7,310,895 B2 | 12/2007 | Whittlesey et al. |
| 7,426,873 B1 | 9/2008 | Kholwadwala et al. |
| 2006/0248965 A1 | 11/2006 | Wyatt et al. |
| 2006/0270951 A1 | 11/2006 | Ikeuchi |
| 2007/0287596 A1* | 12/2007 | Case et al. .................. 482/8 |
| 2010/0036639 A1* | 2/2010 | Vock et al. .................. 702/142 |

OTHER PUBLICATIONS

Frank, R., "Engineering Feat: Adidas engineers integrate a microcontroller, motor and lead screw, and Hall-effect sensor into the sole of a running shoe", Design News, Sep. 27, 2004, http://www.designnews.com/article/print/2955-Engineering_Feat.php.

* cited by examiner

SYSTEM AND METHOD FOR MEASURING POWER GENERATED DURING LEGGED LOCOMOTION

STATEMENT REGARDING FEDERALLY SPONSORED RESEARCH OR DEVELOPMENT

The invention described herein was made in the performance of official duties by employees of the Department of the Navy and may be manufactured, used and licensed by or for the United States Government for any governmental purpose without payment of any royalties thereon.

BACKGROUND AND SUMMARY OF THE INVENTION

The present invention relates generally to a system and method for measuring power during an activity such as legged locomotion. Using power as a means to quantify the level of effort or work exerted over time during activities such as walking or running may be useful in the fields of physical therapy, medicine, athletics, and other physiological research.

Conventional activity monitoring systems focus on the metrics of speed, distance traveled, and heart rate. Such conventional systems have limitations. For example, at a constant level of effort, speed and heart rate can vary widely due to other factors. Heart rate may vary due to a level of hydration or state of recovery, temperature and elevation. Speed may vary with slope of the surface being traversed, such as when a runner is going uphill. Wind speed or other environmental conditions also affect speed.

Conventional activity monitoring systems include sensors located in or on footwear to detect speed and/or distance traversed by a user. Some conventional systems include an array of force sensors located within the footwear to measure forces exerted during human locomotion. These measured forces are used to assist with the design and manufacture of shoes or running surfaces. Force sensors may also be used to measure speed, distance, or jump time of a user. Other conventional systems for monitoring legged locomotion use one or more accelerometers coupled to footwear of a user. Such accelerometer-based systems also measure speed and distance of the user during activity.

The system and method of the present disclosure provides a measurement of power exerted by a body during legged locomotion. In the present system and method, both force sensors and acceleration sensors are provided. Outputs from both the force sensors and the accelerometers are then used to calculate power generated by the body during legged locomotion. Power generated is a more useful factor to monitor than speed, acceleration, or force. The present system and method may be used by a plurality of different users including humans, animals, or legged machines such as robots which undergo legged locomotion. The calculated power may be provided to various output devices, such as a display, or stored for the duration of an exercise activity and analyzed later.

In an exemplary embodiment of the present disclosure, a method is provided for calculating power generated by a body during legged locomotion. The method comprises providing at least one accelerometer to measure acceleration of the body during legged locomotion, providing at least one force sensor to measure a plurality of propulsive force impulses created by the body during legged locomotion, and calculating the power generated by the body during legged locomotion using output signals from both the at least one accelerometer and the at least one force sensor.

In another exemplary embodiment of the present disclosure, a system is provided to calculate power generated by a body during legged locomotion. The system comprises at least one accelerometer to measure acceleration of the body during legged locomotion, at least one force sensor to measure a plurality of propulsive force impulses created by the body during legged locomotion, and a processor configured to calculate the power generated by the body during legged locomotion using output signals from both the at least one accelerometer and the at least one force sensor.

BRIEF DESCRIPTION OF THE DRAWINGS

The foregoing aspects and other features of this invention will become more readily appreciated and better understood by reference to the following detailed description when taken in conjunction with the accompanying drawings in which.

DETAILED DESCRIPTION OF THE DRAWINGS

Figure 1:
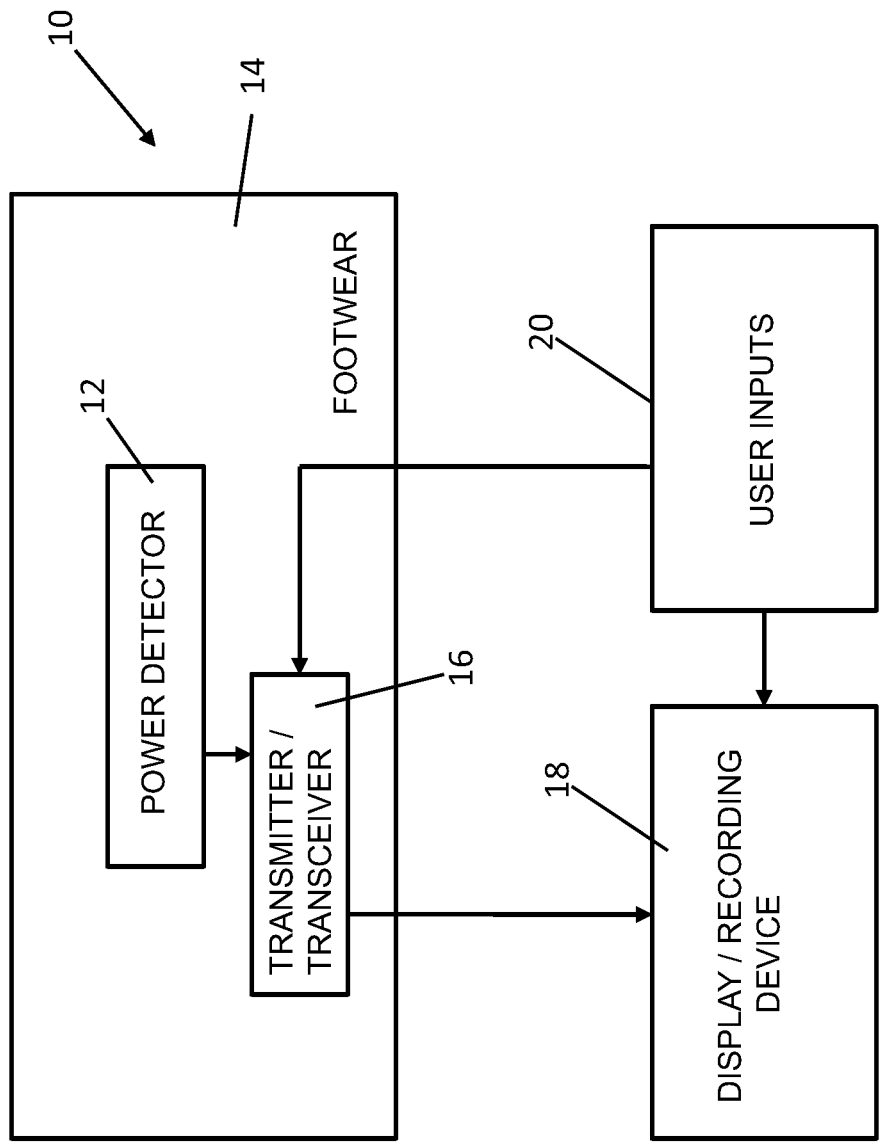
FIG. 1 is a block diagram of an illustrated embodiment of a power detector for detecting power generated during a legged locomotion of a body.

For the purposes of promoting an understanding of the principles of the invention, reference will now be made to the embodiments illustrated in the drawings, which are described below. The embodiments disclosed below are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates. Corresponding reference characters indicate corresponding parts throughout the several views.

Referring to FIG. 1, a first illustrated embodiment of the present disclosure is shown. A system 10 includes a power detector 12 configured to be located within the footwear 14 worn on a foot or other appendage of a body. As discussed above, the term "body" used herein refers to a human, an animal or a machine, such as a robot, which undergoes legged locomotion. The power detector 12 coupled to footwear 14 calculates power generated by the body during legged locomotion such as walking or running.

In the embodiment of FIG. 1, power is calculated by the power detector 12 and transmitted by a transmitter or transceiver 16 to a remote display/recording device 18. In an illustrated embodiment the transmitter/transceiver 16 and the other components of the power detector 12 are included in an integrated device or ASIC. In this embodiment, power detector 12 outputs a signal indicating calculated the power in Watts generated by the body during legged locomotion. The power output may be displayed on a display 18 or stored in a memory of display/recording device 18 for future analysis. The display/recording device 18 may be, for example, a watch-type device worn by the user, eyeglasses worn by the user that have an integrated display, or any other suitable device. As discussed below, device 18 may allow the user to receive cues such as notifications that certain upper and lower power limits are being met. Such cues may be provided either audibly or visually during an exercise activity without distracting the running or walking stride of the user. In the FIG. 1 embodiment, user inputs 20 are provided to allow a user to control the system 10 to provide inputs to the power detector 12 and/or the display/recording device 18 such as the weight of the body to calibrate the system as discussed in detail below. The user inputs 20 may be integrated with the display/recording device 18 or they may be separate inputs.

Figure 2:
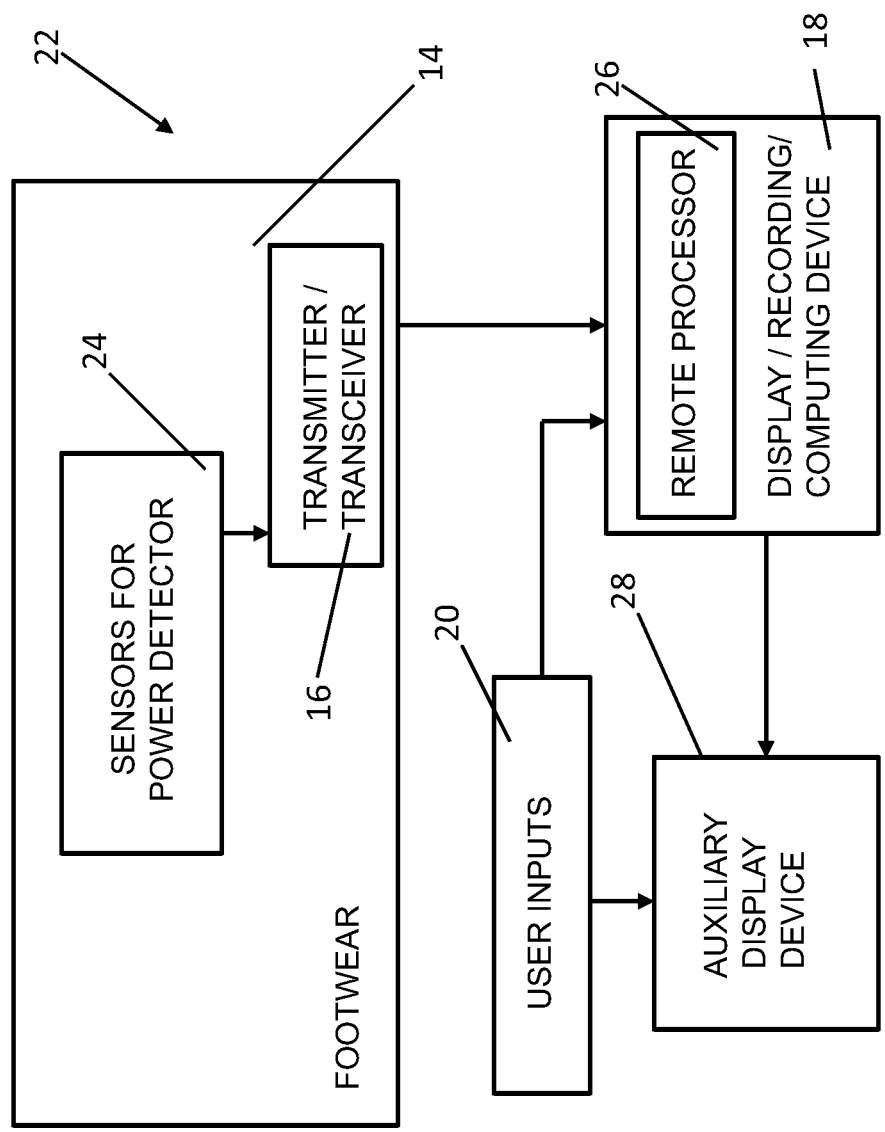
FIG. 2 is a block diagram illustrating another embodiment of a power detector.

FIG. 2 illustrates another embodiment of the present invention. In this embodiment, sensors 24 for the power detector are located within footwear 14. Output(s) from the sensors 24 are transmitted by a transmitter or transceiver 16 to a remote processor 26. In an illustrated embodiment the transmitter/transceiver 16 and the other components of the power detector sensors 24 are included in an integrated device or ASIC. The remote processor 26 is illustratively a component of a display/recording device 18. The display/recording/computing device 18 may be a watch-type device worn by the user. A separate auxiliary display device 28 may receive data from device 18 for display. The auxiliary display device 28 may be eyeglasses having an integrated display, for example, as discussed above. User inputs 20 may be provided to the display/recording/computing device 18 or the auxiliary display device 28. The embodiment of FIG. 2 transmits output signals from sensors, such as accelerometers 40 and force sensors 44 discussed below, to processor 26 for the final power calculation. By providing remote processing on processor 26, power consumption by the sensor components 24 within the footwear 14 may be reduced.

In the embodiments of FIGS. 1 and 2, the power detector 12 or sensors 24 for the power detector may be located in one shoe or other footwear item worn by the body. For human legged location, for example, having power detected by power detector 12 in footwear 14 on only one leg provides only half of the propulsion force generated by the body. Therefore, power may be estimated by multiplying the calculated power from power detector 12 or processor 26 by a factor of two for humans. Another factor may be used for four legged animals.

Figure 3:
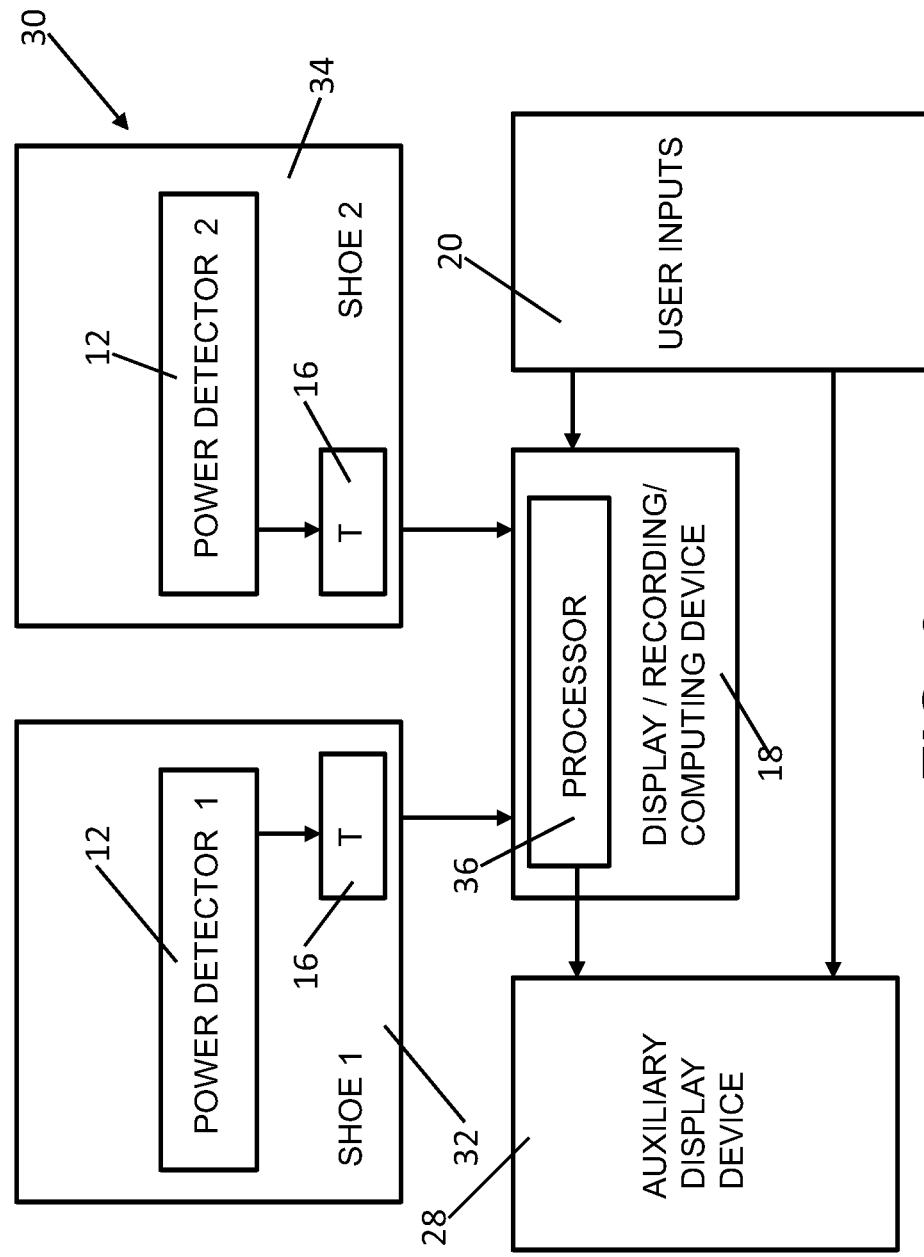
FIG. 3 is a block diagram illustrating yet another embodiment of a power detector.

FIG. 3 illustrates another embodiment of the present invention in which a system 30 includes a first power detector 12 located in a first shoe 32 and a second power detector 12 located within a second shoe 34. By summing outputs from the power detectors 12 in both shoes 32, 34, the total power generated by the human body may be determined. A signal representing power detected by both power detectors 12 is transmitted by transmitters or transceivers 16 to a processor 36 or display/recording/computing device 18 which sums the power detected by both power detectors 12. In an alternative embodiment, sensors 24 may be provided in shoes 32, 34 and the remote processor 36 calculates the power as described above. Processor 36 may communicate with an auxiliary display device 28 as discussed above. User inputs 20 may be provided to the display/recording device 18 or the auxiliary display device 28. In an alternative embodiment, processor 36 may be contained in one of the shoes 32 or 34, if desired.

Figure 4:
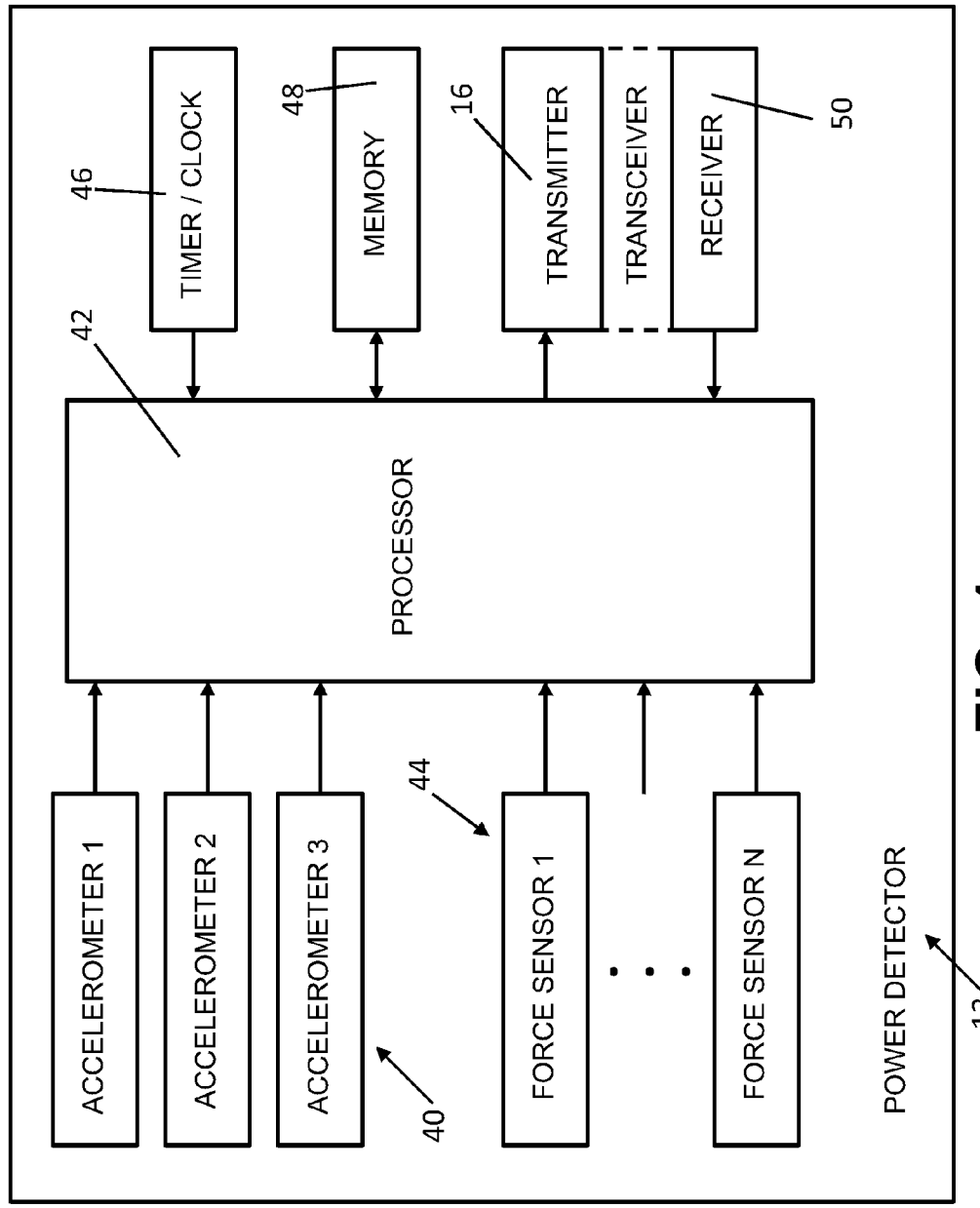
FIG. 4 is a block diagram illustrating further details of one embodiment of the power detector of the present invention.

An illustrated embodiment of the power detector 12 of FIG. 1 is shown in FIG. 4. Power detector 12 includes at least one accelerometer 40 for detecting acceleration of the body. Illustratively one to three accelerometers 40 may be used as part of the power detector 12. An exemplary single accelerometer embodiment which may be used is described in U.S. Pat. No. 6,356,856, which is incorporated herein by reference. For more accurate power detectors 12, three accelerometers 40 are used to measure acceleration in X-axis, Y-axis, and Z-axis directions. Exemplary three accelerometer embodiments which may be used are described in U.S. Pat. No. 5,955,667; 6,301,964; or 6,513,381, which are incorporated herein by reference. Outputs from the accelerometers 40 are coupled to a processor 42. An A/D converter and an amplifier may be coupled between the accelerometers 40 and processor 42.

The power detector 12 also includes at least one force sensor 44. Illustratively two to four pressure sensors 44 are used at locations spaced relative to a foot of the body. For example, in a four force sensor embodiment, force sensors 44 may be placed on medial and lateral sides of the foot, as well as near the heel and the ball of the foot. For increased accuracy and more analysis capability, a greater number of force sensors 44 may be provided. For example an array of 9-12 force sensors 44 located in the footwear 14 increases the accuracy of force measurements during legged locomotion. Any suitable force or pressure sensors 44 may be used in the power detector 12. For example, force sensors described in U.S. Pat. No. 4,814,661; 5,373,651; 5,925,001; or 7,426,873; the disclosures of which are incorporated by reference herein, may be used as force sensors 44. Outputs from force sensors 44 are coupled to processor 42. A/D convertors and amplifiers may be coupled between force sensors 44 and processor 42, if necessary.

Power detector 12 further includes a timer or real time clock 46, a memory 48, and a transmitter 16. Certain embodiments of the power detector 12 may also include a receiver 50. In these embodiments, a transceiver 16 is typically provided. The timer or clock 48 provides timing information to the processor 42. Memory 48 stores software as discussed below accessible by the processor 42 to perform power calculations or other functions. The power generated by the body or other data may be stored in memory 48 for later retrieval and analysis. In an illustrated embodiment, the transmitter/transceiver 16 is integrated into a single communication device or ASIC. Clock 46 and memory 48 may be integrated with the processor 42. A/D convertors may be included as needed.

In an illustrated embodiment, the processor 42 is coupled to transmitter/transceiver 16 which transmits the power data to a remote location preferably by wireless transmission. Instead of the transmitter 16, a port may be provided for connecting the power detector 12 to a remote display/recording/computing device 18 via a wired connection. Typically, such wired connection is done after the activity and the data is retrieved from memory 48. Power detector 12 may also have a receiver 50 to receive wireless data transmissions from a remote device. Receiver 50 is coupled to processor 42. Therefore, receiver 50 can receive inputs from user inputs 20 or the display/recording device 18 to change modes of operation, provide input parameters such as the weight of the body, or provide other desired inputs to the power detector 12. In an illustrated embodiment, a commercially recognized wireless communication protocol is used by transmitter 16 and receiver 50 so that the power detector 12 is compatible with existing activity monitor products. For example, the ANT+ communication protocol may be used by transmitter 16 and receiver 50.

Illustratively, power is calculated by processor 42 of power detector 12 according to the following equation:

$$P = \frac{Fd}{t}$$

Power (P) is work (a force applied over a distance) done in a period of time

Force (F) exerted through a foot during running, walking or other activity results in a reactive movement of the human, animal or machine. Illustratively a plurality of propulsive force impulses are measured by the force sensors 44.

A Distance (d) is traveled by the foot as a consequence of the aforementioned force (F). This distance is illustratively measured using accelerometers 40, wherein the processor 42 performs a double integration function on the acceleration signal to determine distance.

Time (t) is calculated between force impulses and provides the last variable necessary for a power calculation.

In an illustrated embodiment, the distance traveled variable (d) may be estimated by the previously measured distance because any two successive steps are generally similar in length. The body being tested is assumed to be unrestrained. Therefore, if the force measured by the force sensors is greater than the known mass the body, the body is considered to be accelerating. If the detected force is zero, than the body's foot is considered to be off the ground. For example, the body may be airborne during the running mode and/or supported by another foot during walking movement. When measuring power using just one foot, only half of the total propulsive force is measured. Total power is estimated by multiplying by two for humans or by another factor for four legged animals. Due to movement and flexure of the foot relative to the ground, propulsive forces are generally normal to a plane of the foot.

Figure 5:
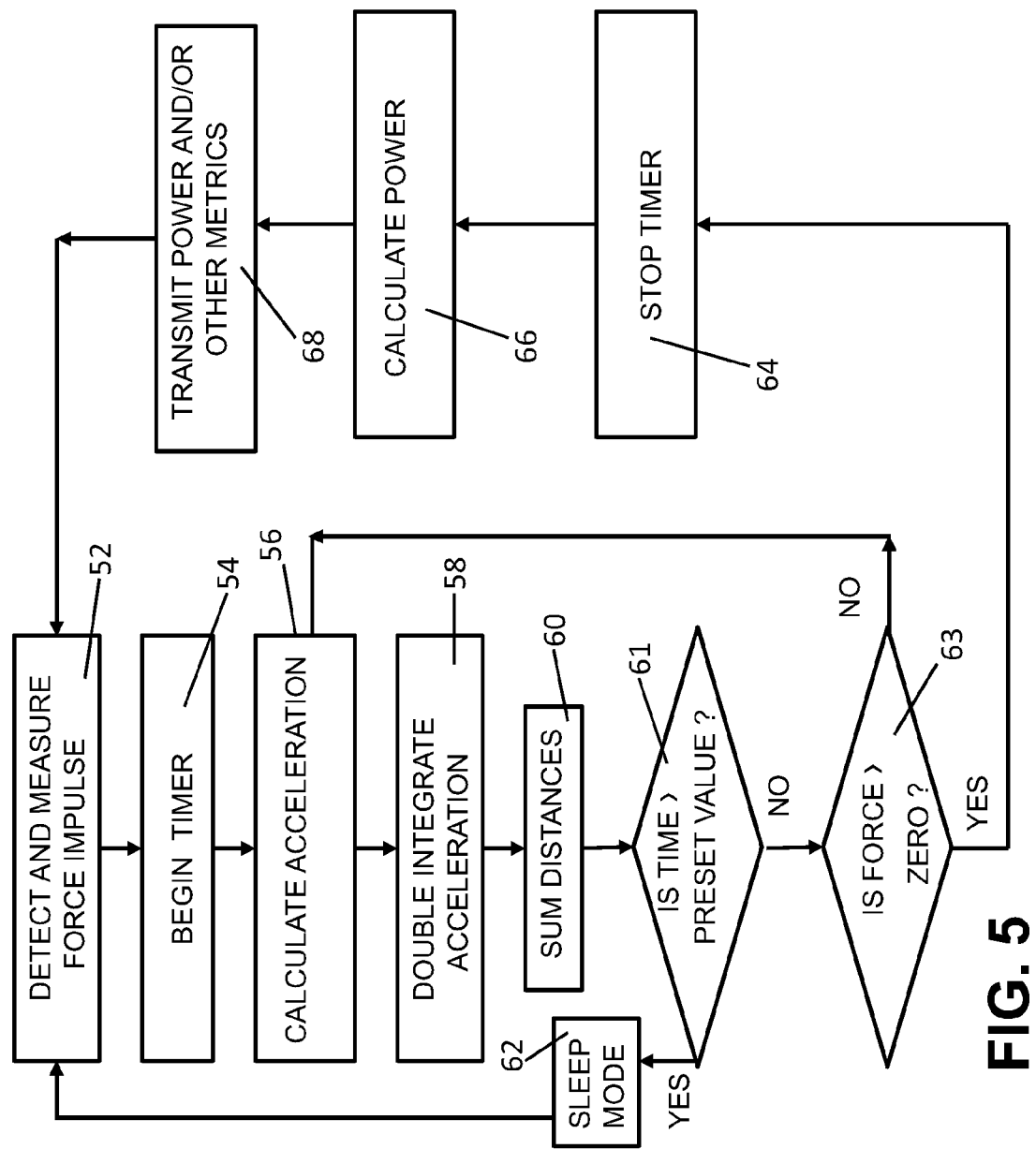
FIG. 5 is a flow chart illustrating steps performed by the power detector in accordance with an illustrated embodiment.

FIG. 5 is a flowchart illustrating the steps performed by processor 44 when calculating power. A force impulse is first detected by the plurality of force sensors 44 and measured as illustrated at block 52. After the force impulse is measured, processor 42 starts the timer 46 as illustrated at block 54 to begin timing the elapsed time between successive force impulses which is the time between strides during legged locomotion. Next, processor 42 calculates acceleration based on inputs from accelerometers 40 as illustrated at block 56. In an illustrated embodiment, processor 42 provides a double integration function on the acceleration output from the accelerometers 40 to calculate a distance moved by the body as illustrated at block 58.

The distance calculated at block 58 is summed to provide an overall distance traveled since the previous force impulse was detected as illustrated at block 60. Processor 42 then determines whether the elapsed time has exceeded a preset value, such as 5 seconds for example, as illustrated at block 61. If so, the processor enters a sleep mode as illustrated at block 62. The detection of another force impulse at block 52 causes processor 42 to exit the sleep mode and begin the process again. If the elapsed time has not exceeded the preset value at block 61, processor 42 then determines whether the force detected by force sensors 44 is greater than zero as illustrated at block 63. If the detected force is not greater than zero at block 63, this indicates that the user's foot is still off the ground, so the processor 42 returns to block 56 to continue calculating the acceleration and sum the total distance traveled.

If the force is greater than zero at block 63, this indicates a new force impulse has been generated by the footwear 14 striking the ground. Processor 42 then stops the timer for the current stride as illustrated at block 64. Therefore, processor knows the force for a particular stride as measured at block 52, the distance for the stride as measured at blocks 56-60, and the time of the stride as determined at block 64. Therefore, using the equation above, processor 42 calculates power generated by the body during the current stride of legged locomotion as illustrated at block 66. The calculated power may be transmitted to a remote display/recording device 18 by transmitter 16 as illustrated at block 68. Other metrics such as cadence, distance traveled, and/or velocity may also be calculated and transmitted at block 68. Processor 42 measures the force impulse which triggered a "Yes" response at block 63 to begin the loop again at block 52.

Figure 6:
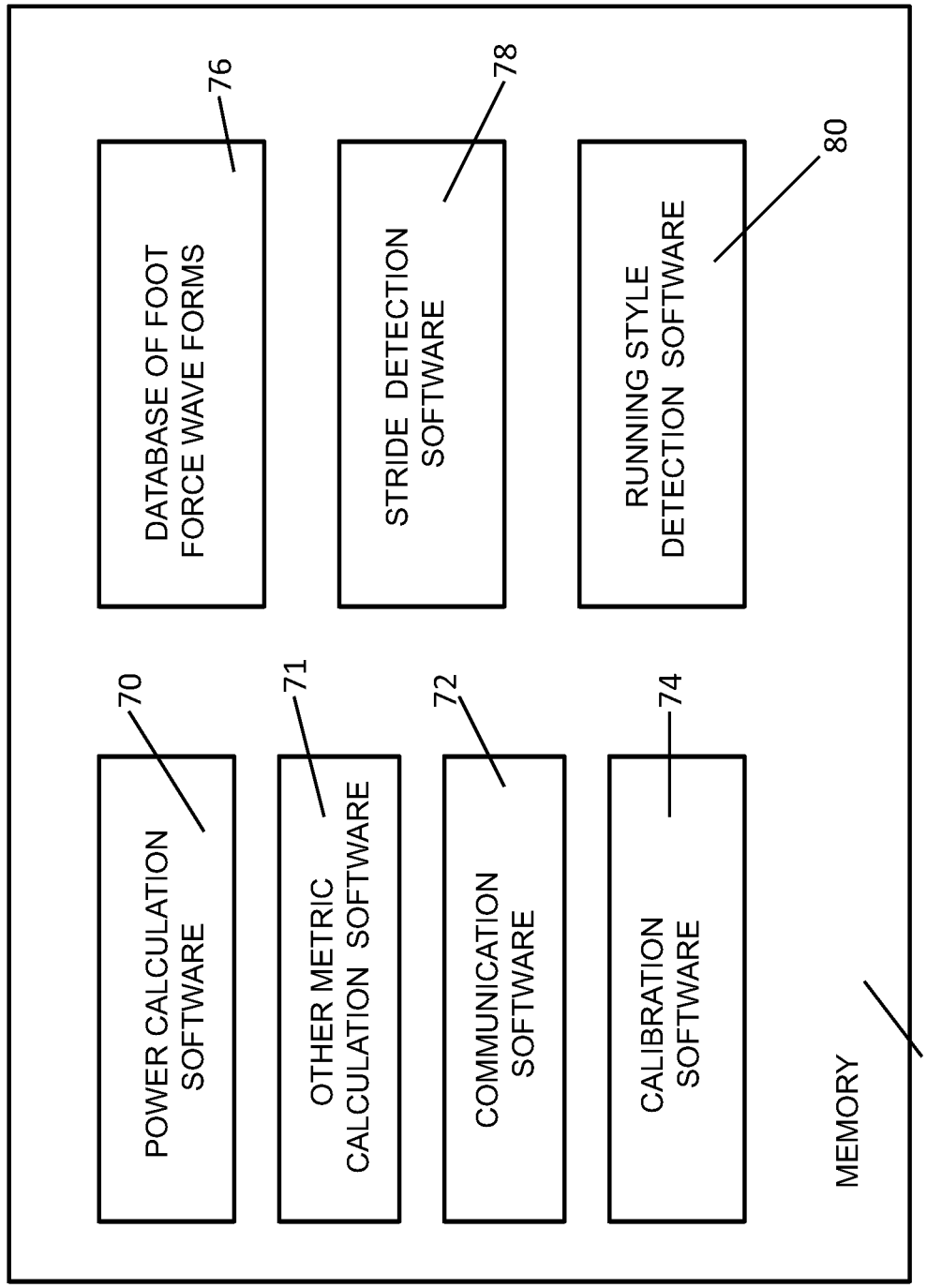
FIG. 6 illustrates software stored in a memory of the power detector.

As discussed above, processor 42 has access to memory 48 and executes software stored in the memory 48 of power detector 12. As illustrated in FIG. 6, memory 48 includes power calculation software 70, other metric calculation software 71, communications software 72, and calibration software 74. Metric calculation software 71 may calculate other metrics such as cadence, distance traveled, velocity and the like. The communications software 72 initializes and configures the communication device/ASIC. Once running, communication may occur by writing a value to be transmitted to a register. Memory 48 may also include a database 76 of foot force wave forms. This database 76 may include sample force wave forms (output signals from force sensors 44) generated by users under various conditions to help analyze force wave forms received from the pressure sensors 44. Memory 48 may also include stride detection software 78 and running style detection software 80 as discussed below. Database 76, stride detection software 78 and running style detection software 80 are preferably stored in memory 100 of display/recording/computing device 18 as discussed below.

Figure 7:
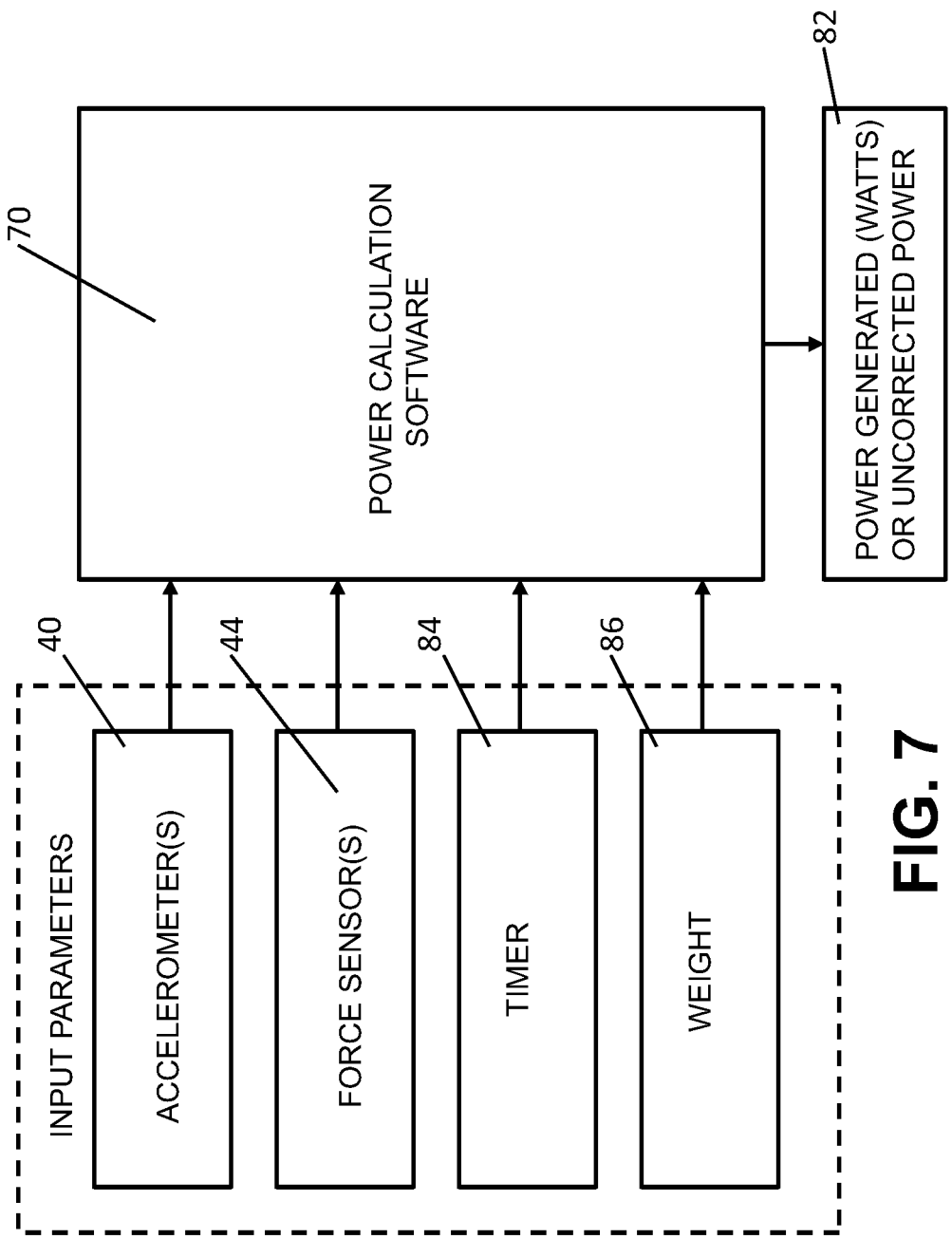
FIG. 7 illustrates a plurality of input parameters for an exemplary embodiment of power calculation software.

Illustrative input parameters to power calculation software 70 are shown in FIG. 7. As discussed above, the power calculation software 70 uses inputs from the accelerometers 40 and force sensors 44 to calculate the power generated by the body. The power generated (in Watts) is provided as an output from the power calculation software 70 as illustrated at block 82. For the FIG. 2 embodiment, an uncorrected power value may be transmitted for processing by the display/recording/computing device 18. In alternative embodiments, the power calculation software may receive inputs from a timer 84. In addition, a weight of the body may be used as an input parameter for calibration as illustrated at block 86.

Communication software 72 stored in memory 48 provides communication between the processor 42 and the remote display/recording/computing device 18 via transmitter 16 and/or receiver 50. As discussed above, communications software 72 uses a conventional communication protocol such as ANT+ for communicating with remote devices.

Calibration software 74 stored in memory 48 is executed by the processor 42 to calibrate force sensors 44 to the known weight of the user. The weight may be input to the force detector 12 using various user inputs 20 discussed above. When the force detected by force sensors 44 is greater than a known mass of the body, processor 44 determines that the body is in motion. The calibration software 74 therefore provides a scaling factor that is used to correct the power calculation and determine when the body is in motion. Further details of calibration are discussed below.

Figure 8:
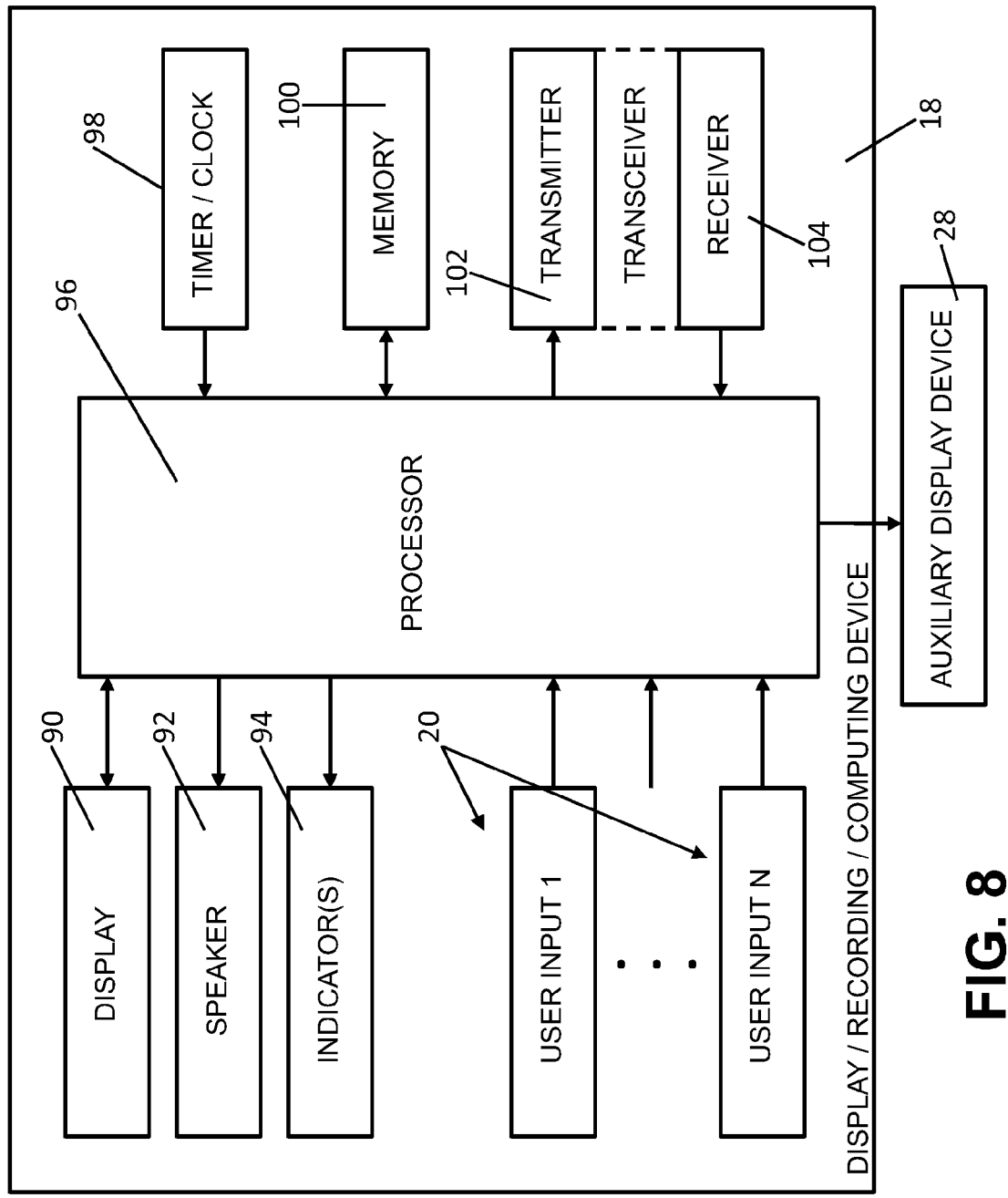
FIG. 8 is a block diagram illustrating details of a display, recording, or computing device in accordance with an illustrated embodiment of the present invention.

FIG. 8 illustrates an exemplary display, recording, and/or computing device usable with the force detector of the present disclosure. As discussed above, the device 18 may be a watch-type device worn by a user during the activity. The device 18 illustratively includes a display 90, a speaker 92 and/or other indicator 94. Indicator 94 may be lights, vibration devices, or other suitable indicators. The display/recording/computing device 18 may also include the plurality of user inputs such as push buttons, a key pad, a touch screen, or other inputs. Inputs 20 are coupled to a processor 96. Processor 96 is also coupled to display 90, speaker 92, and other indicators 94. Processor 96 may also be coupled (preferably wirelessly) to an auxiliary display device 28, such eyeglasses with an integrated display worn by the user, or other suitable display.

Device 18 may also include a timer or real time clock 98, a memory 100, a transmitter 102, and a receiver 104. Illustratively, a transceiver provides the function of transmitter 102 and receiver 104. Timer or clock 98 provides timing information to the processor 96. Memory 100 stores software or databases accessible by the processor 96 to perform a plurality of functions. Transmitter 102 allows device 18 to send information to a remote location such as to another computing device, the auxiliary display device 28, or to the power detector 12. Receiver 104 allows device 18 to receive information such as power data from power detector 12. Memory 100 illustratively stores data/recording device software illustrated at block 106 in FIG. 9. The data/recording device software 106 is accessible and executable by the processor 96 to perform various functions and to provide outputs to the display 90 or 28 or for storage in databases of memory 100.

Figure 9:
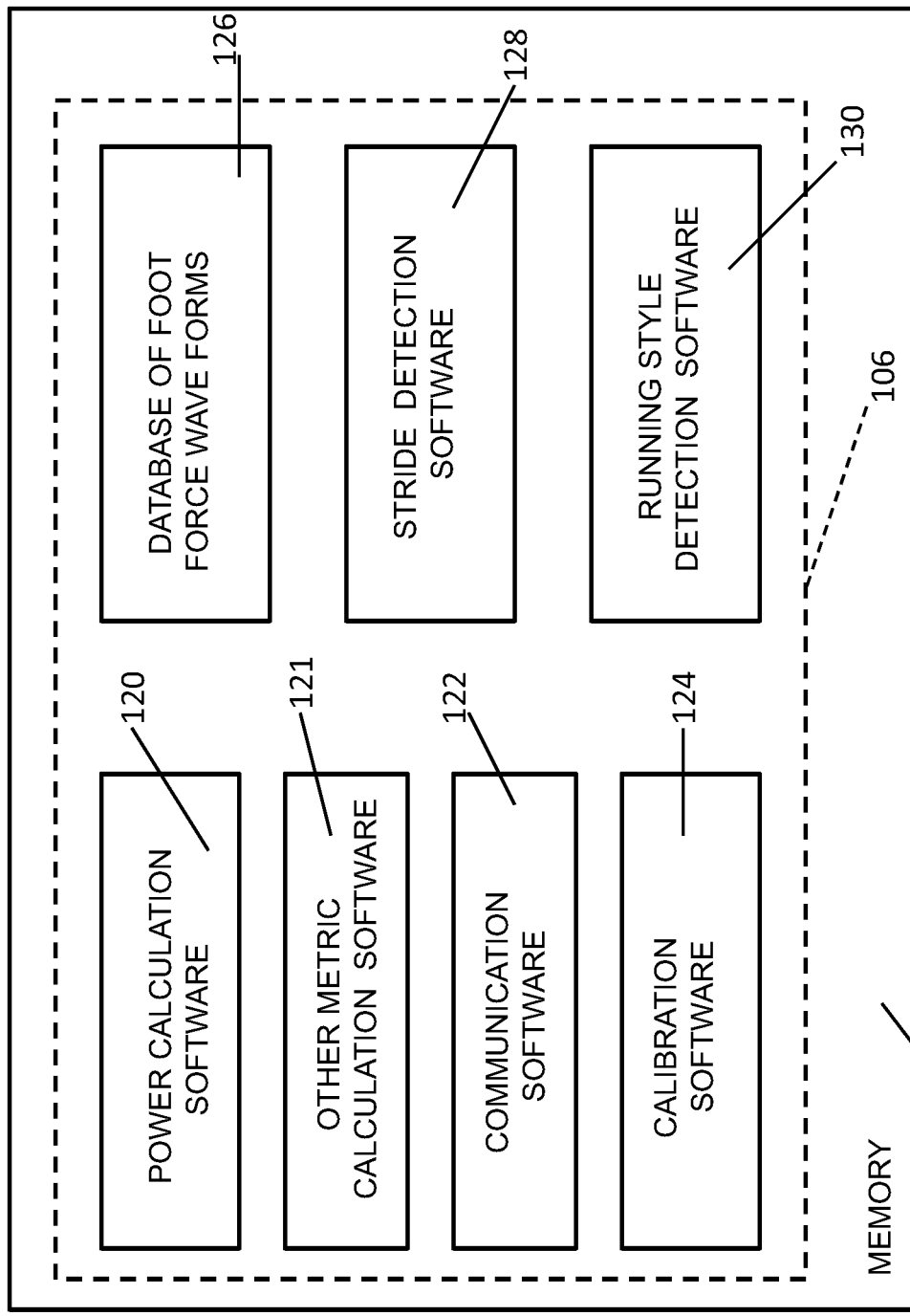
FIG. 9 illustrates software stored in a memory of the display, recording, or computing device.
Figure 10:
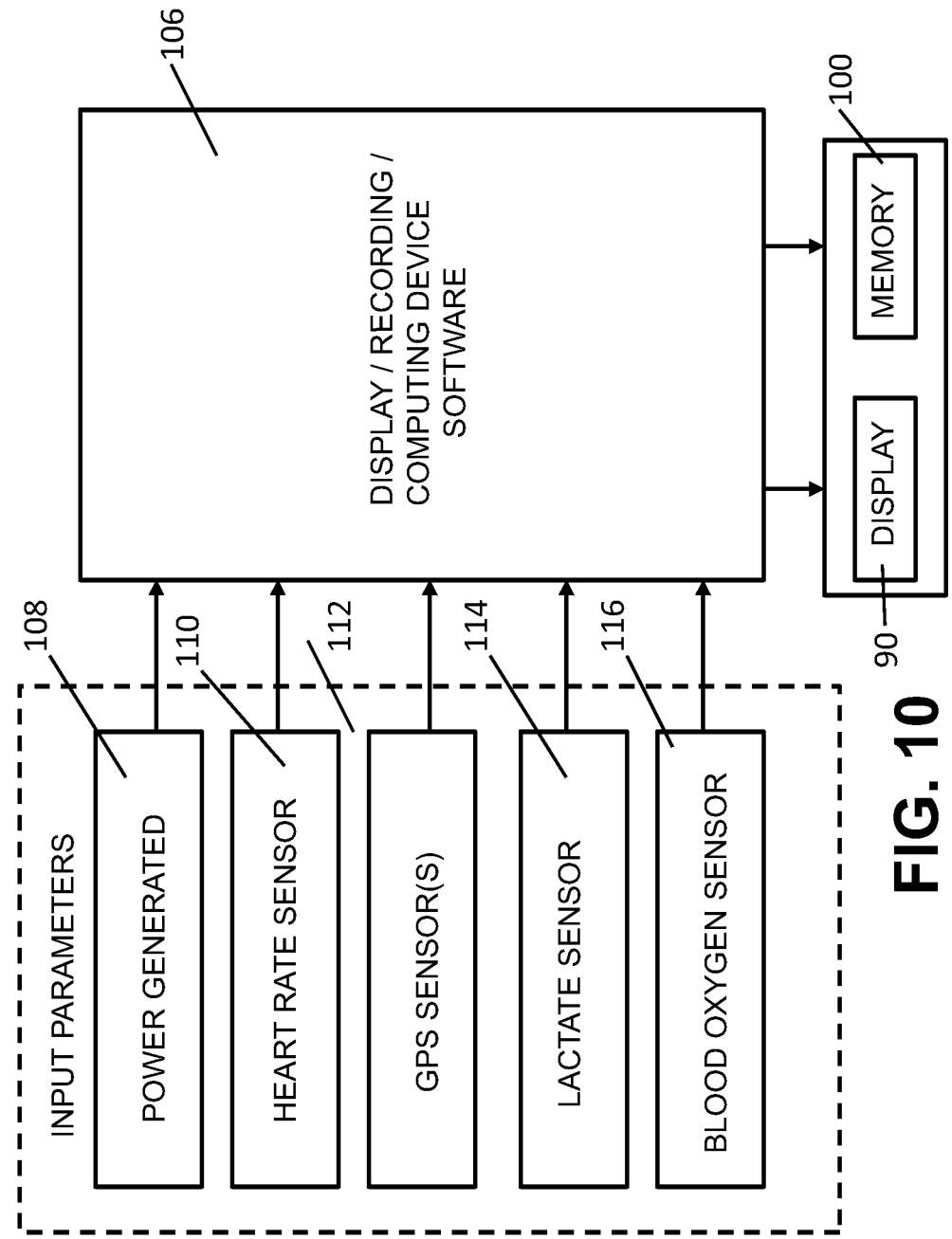
FIG. 10 is a block diagram illustrating exemplary input parameters for display, recording and/or recording device software.

As discussed above, processor 96 has access to memory 100 and executes display/recording/computing device software 106 stored in the memory 100 of display/recording/computing device 18. As illustrated in FIG. 9, display/recording/computing device software 106 stored in memory 100 includes power calculation software 120, other metric calculation software 121, communications software 122, and calibration software 124. Metric calculation software 121 may calculate other metrics such as cadence, distance traveled, velocity and the like. The communications software 122 initializes and configures the communication device/ASIC. Once running, communication may occur by writing a value to be transmitted to a register. Memory 100 may also include a database 126 of foot force wave forms. This database 126 may include sample force wave forms (output signals from force sensors 44) generated by users under various conditions to help analyze force wave forms received from the pressure sensors 44. Memory 100 may also include stride detection software 128 and running style detection software 130 as discussed below.

Stride detection software 128 stored in memory 100 is accessible by the processor 96 to provide a self-correcting algorithm which determines whether the body is in a walking stride or a running stride. Dynamics and force wave forms vary according to the mode of locomotion, such as whether the body is running or walking Stride detection software 128 may access foot force wave forms stored in database 126 to compare the current force signals from force sensors 44 and determine whether the body is walking or running.

Running style detection software 130 stored in memory 100 is accessible by the processor 96 to provide a self-correcting algorithm for the force calculation based on a running style of the body being tested. Different dynamics and force wave forms are generated by flat-footed runners, heavy heel strikers, or runners that run on the balls of their feet. The type of running style may be entered using an user input 20 or may be determined automatically by the running style detection software 130. Running style detection software 130 may access foot force wave forms stored in database 126 to determine the running style of the particular user and compensate or adjust the power calculation based on the running style.

FIG. 9 illustrates input parameters that may be provided to the display/recording device software 106. The output from power detector 12 is a power generated input 108. The display/recording device software 106 may also receive inputs from a heart rate sensor 110, a GPS sensor 112, a lactate sensor 114, and/or a blood oxygen sensor 116. The display/recording device software 106 may link the power calculated by power detector 12 to the heart rate, location, lactate level, and/or blood oxygen level data of the user to permit a detailed analysis of the exercise activity by comparing different physiological parameters to the power generated by the body. The power generated may also be linked to a map via the GPS sensors to provide a visual indication of power expended at various locations during running a particular route.

One illustrated force sensor configuration includes at least one sensor located under the heel of the foot and at least one sensor located under the forefoot. To maintain an acceptable level of accuracy, a calibration of the system may be performed by calibration software 74, 124. One illustrated embodiment includes three calibration modes, two modes for the force sensor array 44 and one mode for velocity/distance measurement sensors 40. A first calibration mode is performed at less regular intervals (such as upon initial setup, after battery changes, or when deemed necessary by the user). This first calibration mode is a two-point calibration adjusting the measurement system to two datums. The first datum is zero force. Illustratively, the user uses user inputs 20 to put the controller into the first calibration mode. The user is then prompted to jump (up to three times possibly) and the system uses the minimum voltages from the force sensors 44 as a zero force set point. Next, the user is prompted to enter the user's weight using the user input 20. Once entered, the user is prompted to stand in place. The aggregate force from force sensors 44 is computed and a calibration coefficient is calculated based on the user weight. A second calibration mode is also performed at less regular intervals such as upon initial setup, after battery changes, or when deemed necessary by the user. The second calibration mode provides a correction coefficient to the speed/distance measurement from sensors 40. When prompted, the user selects a distance to run, such as a 400 m or 5 km course, and begins to run. Upon conclusion of the run, the system obtains a calibration coefficient based on a comparison of the actual distance to the calculated distance. The third calibration mode provides a calibration of the system prior to each use and is initiated automatically. When prompting the power detector 12 to start measurement and after communication with the sensors is initiated, the user's weight will be validated and the user's prompted to stand in place. This will provide an updated single point calibration of the force sensor array 44.

The recent prevalence of miniature sensors and integrated communication ASICS provides many options for the components of the insole sensor devices 12, 16, 24. However, the integration of these components into a package presents some challenges. An insole installed inside a shoe and used during running introduces a hostile environment that includes high levels of shock and moisture among other environmental concerns. The integration of a wireless communication device makes this all the more challenging. The salient characteristics of the insole device are low mass, flexibility of the forefoot area of the insole, and the ability to survive the intended environment. In one embodiment, the user may replace a battery in the footwear. An illustrated embodiment includes a compact circuit board that contains power devices, a small MCU, the accelerometers 40, the communication ASIC, the battery, connection to an antenna, and connection to the force sensors 44. This circuit board is illustratively located in a midfoot area of the insole. The circuit board is not intended to be a serviceable item. Therefore, the assembly may be potted to increase the reliability. The section of the midfoot where this assembly is installed should be reasonably stiff to protect the electronics from flexure and may be integrated into an injection-molded plastic structure. The remainder of the insole assembly may be made of an elastomeric material to accommodate flexure of the user's foot. An illustrated method of manufacture comolds the electronics package, antenna, and force sensors 44 into a single assembly. Preferably this assembly is podiatrically neutral, thin throughout, and does not interfere with the user's choice of insole which includes orthotic inserts. Further, this insole may be molded in a limited number of sizes (2-3 sizes) to accommodate a range of foot sizes. A single size may not be possible because location of the force sensors relative to the geometry of the foot is necessary. However, a small number of different sizes may provide compatibility with the greatest number of users and maximize accuracy. The insole may have a range of "adjustment" to provide the proper fit by means of trimming the forward edge of the insole.

A challenge for the power measurement system is the difference in biomechanics between running and walking and the desire to accurately measure power generated during both modes of locomotion. Upon initialization and commencement of the workout, the system determines the mode of locomotion. Running locomotion has a ballistic phase where both feet are off the ground at one point. It is assumed that most users of this system will be running, so the default algorithm is for running. However, during each measurement cycle (of two steps/strides) the system will determine if there was a ballistic phase (a point where $F_{left}=0$ AND $F_{right}=0$). If there is no ballistic phase, the walking algorithm will be used. Again, during the walking algorithm, the system will look for a ballistic phase and will choose the appropriate mode. The force and speed measurement of the two modes of locomotion are the same. Force and speed data looks much different for these modes especially when overlaid for both feet. Prompt discrimination by the algorithms maintains accuracy.

A challenge exists in the measurement of foot velocity and displacement in accelerometer based systems that currently exist on the market. The present system benefits from having pressure/force measurements on the foot. By using references on the pressure signal, isolation of the desired acceleration data from accelerometers 40 is obtained. Integration of the signal illustratively commences when the sum of pressure sensors 44 for one foot is equal to zero. Integration stops (average velocity and distance data for the foot movement) when a pressure greater than zero is recorded. Noise will exist on the pressure signals so it may be necessary to substitute a fraction of user weight for zero in the algorithm. For example, the acceleration integration may begin when the force sensor reading is <25% of the user's weight and the integration may stop when the force sensor reading is >25% of the user's weight.

The present system may calculate the force impulse exerted during the drive phase of running which is used to perform the power calculation. The drive phase is preceded by the support phase whereby the foot lands on the running surface and results in a force imparted normally through the foot. This force is not propulsive and can be characterized as an inelastic collision when the runner loses kinetic energy. The musculature of the leg performs work to support the runner against the force of gravity and move the runner to the drive phase of the gait. At slower running speeds, there exists a short period between the support and drive phase where the force exerted through the foot (insole device) is equal to the weight of the runner. During the drive phase of the gait, a force is exerted through the supported leg to propel the runner in a ballistic manner. In an illustrated embodiment, the pressure/force impulse of the drive phase may be isolated for the power calculation. However, it is not required. Because power measurement devices for runners are not currently available there is not a standardized method of extracting power from gait dynamics. The software may scale the force impulse (from 0 to 100%) during the power calculation. Individual runners exert unique forces each during the support and drive phases. If the user has access to a running ergometer (treadmill) it is possible to perform a higher level of system calibration.

An illustrative embodiment of the present system includes means for providing software updates to the display/recording/computing device 18, and possibly to the power detector 12. Minimizing the calculation and analysis performed within the power detector insole device 12 may preclude the need for this capability in the insole devices.

While one illustrated embodiment of the power measurement system for legged locomotion is for human beings, a similar system may also be used for equine or other applications. Thoroughbred horses present unique challenges and dynamic field performance data that can be obtained from these "athletes" is limited. A power measurement system may be adapted for equine use by means of a horseshoe that has integrated force and speed measurement. The dynamics for equine locomotion are different and require modified algorithms, but the overall concept is very similar. Structural differences between the feet of humans and the hooves of horses allows a simplified force measurement system for equine use. For example, a single force sensor may suffice.

Depending on the sensors that are used, the controller unit may be able to display in real time such info as: current power, average power (for the workout or interval), pace, cadence, distance traveled, heart rate, lactate level, and elapsed time (for the workout or interval). The unit may provide continuous display of sensor status and whether current power is above or below average power (for the entire workout or interval based on controller mode). Additional information may be available post-workout, preferably once the data is downloaded to a personal computer (PC) containing an analysis software suite.

Part of the PC software suite includes a Symmetry Analysis Module that provides visual depiction of imbalances between the left and right foot. A single plot may simultaneously display on a bar graph: average power (left and right), average force (left and right), average stride length (left and right) and average foot velocity (left and right). This information may be used to diagnose issues with the runner's biomechanics and provide clues for improving running form. Further, changes in the Symmetry Analysis may be indicative of onset of injury or other weaknesses.

Part of the PC software suite may include Efficiency Analysis Module that calculates a unique metric of Pace/Power. This metric may be tracked over time to determine changes in efficiency and make evident areas of inefficiency. Efficiency is variable upon pace. That is to say that a runner is more efficient at marathon distances than 100 m sprints. Additionally, a "specific efficiency" metric can be calculated which divides the efficiency by mass to remove the differences resulting from varying user weights. The present system has the capability to measure the full force impulse containing both support and drive phases of running. As such, a gait that has a large inelastic collision component (lost energy) will increase measured power and result in a lower efficiency given a held speed. If a user has a more economical/efficient gait, these inelastic losses may be reduced and increases in efficiency will be observed/reported.

Part of the PC software suite may also include Physiological Analysis Module that compares physiological measurements obtained from the system (e.g. heart rate and lactate level) to power and speed data. Using the software to compare this data can provide insightful information regarding level of effort/pacing at VO2 max levels and functional threshold levels.

Communication between the sensors, control device, display devices, and computer interface is preferably wireless in nature and preferably uses an existing and successfully adopted communication protocol. One such protocol is called ANT+ and a family of low-power ASICS are available that suit this application.

The preferred control device 18 is a watch-type device worn on a user's wrist. An LCD or LED display may be used to show all desired data in real time. Studies indicate that runners must "break stride" each time they view a wrist device, so an alternate means of conveying information is useful. This could be audible, by other means (vibration), or through an additional auxiliary display device 28 discussed above. The device 18 has sufficient memory 100 to store data from all the sensors 40, 44. Device 18 also has sufficient processing power to derive all parameters displayed in real-time (power, distance, etc). Device 18 further has a means of wireless communication to interface with all sensors 40, 44, display devices, and interfaces to personal computers.

As previously described an additional display device 28 may be integrated into an item such as eyeglasses that provides a continuous display of data that is available to the user without impacting their running performance. This device projects information into the runner's field of vision and maintain wireless communication with the display/recording/computing device 18.

Lactate is a byproduct of anaerobic metabolism and at high levels of intensity increasing levels of lactate limit the performance of an athlete. A "lactate threshold" exists which is usually defined as the level of intensity at which the athlete can possibly sustain for 40 minutes to one hour (also called the functional threshold). Elite athletes have lactate levels measured in blood samples to help ascertain their lactate or functional thresholds. The technology currently exists for individuals afflicted with diabetes to continuously monitor blood glucose levels using a surface mounted subcutaneous sensor that maintains wireless communication with a control device. Similar technology may be used to implement a lactate sensor which is part of this power measurement system.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

The invention claimed is:

1. A method for calculating power generated by a body during legged locomotion comprising:
   providing at least one accelerometer to measure acceleration of the body during legged locomotion;
   providing at least one force sensor to measure a plurality of propulsive force impulses created by the body during legged locomotion by measuring said body's foot contact forces during a drive phase of said body's walking or running; and
   calculating the power generated by the body during legged locomotion using output signals from both the at least one accelerometer and the at least one force sensor, said calculating step comprises utilizing a power equation comprising P=(F*d)/t, where P represents power as force applied over a distance done in a period of time where the measured plurality of propulsive force impulses are exerted from said body's foot contact during said drive phase of said body's walking or running, d is distance traveled by said foot as a consequence of at least one of said plurality of said propulsive forces, and t is time calculated between force impulses;
   determining a running style of said body based on whether said body is in a walking or running stride based on accessing a plurality of foot force wave forms stored in a database and comparing said measured plurality of propulsive forces with said foot force wave forms stored in said database; and
   adjusting a power result generated by said calculating the power generated by the body step based on said running style determination.

2. The method of claim 1, further comprising providing an indication related to the calculated power on an indicator.

3. The method of claim 2, wherein the indicator is a graphical display.

4. The method of claim 2, wherein the indicator is one of an audible indication, a visual indication, and/or a vibration.

5. The method of claim 1, further comprising comparing the power calculated with at least one physiological sensor output signal.

6. The method of claim 5, wherein the at least one physiological sensor is at least one of a heart rate sensor, a blood oxygen sensor, and a lactate sensor.

7. The method of claim 1, wherein three accelerometers are provided to measure acceleration of the body in an X-axis direction, in a Y-axis direction, and in a Z-axis direction.

8. The method of claim 1, wherein at least one accelerometer is used to measure acceleration of the body.

9. The method of claim 1, wherein a plurality of force sensors are located in a spaced apart array and located in a footwear item worn on the body.

10. The method of claim 1, wherein the at least one accelerometer and the at least one force sensor are located in an insole configured to fit within a shoe.

11. The method of claim 1, further comprising transmitting a signal indicative of the calculated power to a remote location.

12. The method of claim 1, wherein calculating the power comprises:
   detecting a plurality of force impulses based on output signals from the at least one force sensor;
   determining the distance traversed between successive force impulses based on output signals from the at least one accelerometer;
   determining an elapsed time between the successive force impulses; and calculating power based upon the magnitude of the force impulse, the distance traversed between successive force impulses, and the elapsed time.

13. The method of claim 1, wherein calculating the power includes providing at least one accelerometer and at least one force sensor on each leg of the body, calculating power generated by each leg of the body, and summing the power generated by the legs to calculate total power generated by the body during legged locomotion.

14. The method of claim 1, wherein output signals from the at least one accelerometer and the at least one force sensor are transmitted to a remote computing device which performs the calculating the power step.

15. The method of claim 1, further comprising calibrating the at least one force sensor based upon a weight of the body.

16. A system to calculate power generated by a body during legged locomotion, the system comprising:
   at least one accelerometer to measure acceleration of the body during legged locomotion;
   at least one force sensor to measure a plurality of propulsive force impulses created by the body during legged locomotion by measuring said body's foot contact forces during a drive phase of said body's walking or running;
   a processor configured to calculate the power generated by the body during legged locomotion using output signals from both the at least one accelerometer and the at least one force sensor;
   determining a running style of said body based on whether said body is in a walking or running stride based on accessing a plurality of foot force wave forms stored in a database and comparing said measured plurality of propulsive forces with said foot force wave forms stored in said database; and
   adjusting a power result generated by said calculating the power generated by the body step based on said running style determination.

17. The system of claim 16, further comprising an indicator coupled to the processor, the indicator providing an indication related to the calculated power on an indicator.

18. The system of claim 17, wherein the indicator is a display.

19. The system of claim 17, wherein the indicator is one of an audible indicator, a visual indicator, and/or a vibrator.

20. The system of claim 16, further comprising at least one physiological sensor coupled to the processor, the processor comparing the power calculated with at least one physiological sensor output signal.

21. The system of claim 20, wherein the at least one physiological sensor is at least one of a heart rate sensor, a blood oxygen sensor, and a lactate sensor.

22. The system of claim 16, wherein three accelerometers are provided to measure acceleration of the body in an X-axis direction, in a Y-axis direction, and in a Z-axis direction.

23. The system of claim 16, wherein a single accelerometer is used to measure acceleration of the body.

24. The system of claim 16, wherein a plurality of force sensors are located in a spaced apart array and located in a footwear item worn on the body.

25. The system of claim 16, wherein the at least one accelerometer and the at least one force sensor are located in an insole configured to fit within a shoe.

26. The system of claim 16, further comprising a transmitter coupled to the processor to transmit a signal indicative of the calculated power to a remote location.

27. The system of claim 16, wherein the processor is programmed with software to detect and measure a plurality of force impulses based on output signals from the at least one force sensor; to determine a distance traversed between successive force impulses based on output signals from the at least one accelerometer; to determine an elapsed time between the successive force impulses; and to calculate power based upon the magnitude of the force impulse, the distance traversed between successive force impulses, and the elapsed time.

28. The system of claim 16, wherein at least one accelerometer and at least one force sensor are located on each leg of the body, and the processor calculates power generated by each leg of the body and sums the power generated by the legs to calculate total power generated by the body during legged locomotion.

29. The system of claim 16, wherein processor is located in a remote computing device spaced apart from the at least one accelerometer and the at least one force sensor, and further comprising a transmitter configured to transmit the output signals from the at least one accelerometer and the at least one force sensor to the remote computing device which calculates the power generated by the body during legged locomotion.

30. The system of claim 16, wherein the processor is programmed with software to calibrate the at least one force sensor based upon a weight of the body.

31. A method for calculating power generated by a body during legged locomotion comprising:
   providing at least one accelerometer to measure acceleration of the body during legged locomotion;
   providing a plurality of force sensors each comprising a transducer that adapted to convert a mechanical force applied to the force sensors by a port of said body into a plurality of electrical signals to measure a plurality of propulsive force impulses created by the body during legged locomotion;
   calibrating the at least one force sensor based upon a weight of the body;
   calculating the power generated by the body during legged locomotion using output signals from both the at least one accelerometer and the at least one force sensor by measuring said body's foot contact forces during a drive phase of said body's walking or running;
   wherein a plurality of force sensors are located in a spaced apart array and located in a footwear item worn on the body;
   determining a running style of said body based on whether said body is in a walking or running stride based on accessing a plurality of foot force wave forms stored in a database and comparing said measured plurality of propulsive forces with said foot force wave forms stored in said database; and
   adjusting a power result generated by said calculating the power generated by the body step based on said running style determination.

32. The method of claim 31, further comprising providing an indication related to the calculated power on an indicator.

33. The method of claim 32, wherein the indicator is a graphical display.

34. The method of claim 32, wherein the indicator is one of an audible indication, a visual indication, and/or a vibration.

35. The method of claim 31, further comprising comparing the power calculated with at least one physiological sensor output signal.

36. The method of claim 35, wherein the at least one physiological sensor is at least one of a heart rate sensor, a blood oxygen sensor, and a lactate sensor.

37. The method of claim 31, wherein three accelerometers are provided to measure acceleration of the body in an X-axis direction, in a Y-axis direction, and in a Z-axis direction.

38. The method of claim 31, wherein a single accelerometer is used to measure acceleration of the body.

39. The method of claim 31, wherein the at least one accelerometer and the plurality of force sensors are located in an insole configured to fit within a shoe.

40. The method of claim 31, further comprising transmitting a signal indicative of the calculated power to a remote location.

41. The method of claim 31, wherein calculating the power comprises:
   detecting said plurality of propulsive force impulses based on output signals from the plurality of force sensors;
   determining a distance traversed between successive force impulses based on output signals from the at least one accelerometer;
   determining an elapsed time between the successive force impulses; and
   calculating power based upon the magnitude of the force impulse of said body's foot contact, the distance traversed between successive force impulses, and the elapsed time.

42. The method of claim 31, wherein calculating the power includes providing at least one accelerometer and a plurality of said force sensors on each leg of the body, calculating power generated by each leg of the body, and summing the power generated by the legs to calculate total power generated by the body during legged locomotion.

43. The method of claim 31, wherein output signals from the at least one accelerometer and the plurality of force sensors are transmitted to a remote computing device which performs the calculating the power step.

* * * * *